(12) United States Patent
Hilario et al.

(10) Patent No.: US 12,708,398 B2
(45) Date of Patent: Aug. 18, 2026

(54) HANDLE ASSEMBLY FOR TISSUE RESECTION DEVICE

(71) Applicant: MINERVA SURGICAL, INC., Santa Clara, CA (US)

(72) Inventors: Estela Hilario, Los Altos, CA (US); Dominique Filloux, Santa Clara, CA (US); Sean Darby, Gilroy, CA (US)

(73) Assignee: Axora Medical, Inc., Sunnyvale, CA (US)

( * ) Notice: Subject to any disclaimer, the term of this patent is extended or adjusted under 35 U.S.C. 154(b) by 558 days.

(21) Appl. No.: 18/161,579

(22) Filed: Jan. 30, 2023

(65) Prior Publication Data

US 2023/0240704 A1 Aug. 3, 2023

Related U.S. Application Data

(60) Provisional application No. 63/304,940, filed on Jan. 31, 2022.

(51) Int. Cl.
*A61B 17/3205* (2006.01)
*A61B 17/00* (2006.01)

(52) U.S. Cl.
CPC .................... *A61B 17/3205* (2013.01); *A61B 2017/00367* (2013.01); *A61B 2017/00424* (2013.01)

(58) Field of Classification Search
CPC .... A61B 2017/2925; A61B 2017/2919; A61B 2017/2912; A61B 2017/2924;
(Continued)

(56) References Cited

U.S. PATENT DOCUMENTS 24,005 A 5/1859 Brooks
54,069 A 4/1866 Hartford
(Continued)

FOREIGN PATENT DOCUMENTS

DE 3804849 A1 9/1988
JP 2003290238 A 10/2003
(Continued)

OTHER PUBLICATIONS

BCMA Medical Museum, Bone Drill Exhibit (1914-1930), BCMA Website http://bcmamedicalmuseum.org/object/993.1220.1 (Feb. 9, 2009 vesion).
(Continued)

*Primary Examiner* — Majid Jamialahmadi
(74) *Attorney, Agent, or Firm* — Seager, Tufte & Wickhem, LLP

(57) ABSTRACT

A handle assembly for a tissue resection device may include a handle including an elongate tubular body defining a central longitudinal axis, and a palm grip extending from the elongate tubular body, the palm grip being configured to be engaged by a palm of a user; a trigger member extending from the elongate tubular body, the trigger member being configured to be engaged by one or more fingers of the user; and a drive mechanism disposed within the elongate tubular body, the drive mechanism being configured to move a tissue resection element extending distally from the elongate tubular body. The trigger member is engaged with the drive mechanism such that translation of the trigger member relative to the handle actuates the drive mechanism. The trigger member is configured to translate parallel to the central longitudinal axis between a first position and a second position.

17 Claims, 10 Drawing Sheets

(58) Field of Classification Search
CPC ...... A61B 17/2909; A61B 2017/00424; A61B 2017/0042; A61B 2017/00367; A61B 17/32002
See application file for complete search history.

(56) References Cited

U.S. PATENT DOCUMENTS 377,783 A 2/1888 Shaver
383,031 A 5/1888 Allgoever
385,414 A 7/1888 Huber
505,165 A 9/1893 Hughes
515,327 A 2/1894 Eggert
532,145 A 1/1895 Defatsch
537,681 A 4/1895 Furbish
543,096 A 7/1895 Jones
560,281 A 5/1896 Rauhoff
568,460 A 9/1896 Schay
575,734 A 1/1897 Rauhoff
597,766 A 1/1898 Furbish
621,401 A 3/1899 Davis
624,122 A 5/1899 Stevenson
652,137 A 6/1900 Olson
654,150 A 7/1900 Hanna et al.
666,508 A 1/1901 Furbish
674,719 A 5/1901 Woodruff
685,678 A 10/1901 Furbish
700,970 A 5/1902 Mcfarland
711,169 A 10/1902 Leblanc
722,332 A 3/1903 Stump
756,388 A 4/1904 May
791,766 A 6/1905 Furbish
791,767 A 6/1905 Furbish
799,968 A 9/1905 Bläske
819,536 A 5/1906 Furbish
873,296 A 12/1907 Chappelle
924,372 A 6/1909 Peck
924,878 A 6/1909 Baron
938,341 A 10/1909 Ruple
942,571 A 12/1909 Leland et al.
942,572 A 12/1909 Leland
973,881 A 10/1910 Rioux
979,939 A 12/1910 Fegley et al.
1,023,023 A 4/1912 Leopold
1,024,960 A 4/1912 Wolin
1,033,615 A 7/1912 Peck
1,054,142 A 2/1913 Plein
1,061,773 A 5/1913 Nahlinger
1,104,210 A 7/1914 Meredith
1,104,863 A 7/1914 Baldwin
1,134,511 A 4/1915 Carlson
1,183,426 A 5/1916 Booth
1,188,162 A 6/1916 Duggan
1,206,589 A 11/1916 Pipshik
1,268,309 A 6/1918 White
1,290,489 A 1/1919 Bauer
1,304,714 A 5/1919 Starrett
1,330,053 A 2/1920 Booth
1,415,251 A 5/1922 McLean
1,415,822 A 5/1922 Fegley et al.
1,422,411 A 7/1922 Borick
1,460,201 A 6/1923 Leopold
1,477,337 A 12/1923 Fegley
1,497,479 A 6/1924 Booth
1,516,443 A 11/1924 Leopold
1,531,086 A 3/1925 Fegley et al.
1,578,866 A 3/1926 Swain
1,704,067 A 3/1929 Wick
1,821,194 A 9/1931 Wilcox
1,838,957 A 12/1931 Orawiec
1,904,679 A 4/1933 Fegley et al.
1,971,289 A 8/1934 Abramson et al.
1,971,290 A 8/1934 Abramson et al.
3,049,018 A 8/1962 Lusskin et al.
3,619,081 A 11/1971 Gruska et al.
3,805,791 A 4/1974 Seuberth et al.
3,811,446 A 5/1974 Lerwick et al.
3,869,936 A 3/1975 Taillardat
3,955,578 A 5/1976 Chamness et al.
4,273,128 A 6/1981 Lary
4,306,599 A 12/1981 Kurahashi
4,343,200 A 8/1982 Alworth et al.
4,345,599 A 8/1982 McCarrell
4,524,650 A 6/1985 Marks
4,611,594 A 9/1986 Grayhack et al.
4,685,344 A 8/1987 Horn et al.
4,694,838 A 9/1987 Wijayarthna et al.
4,850,957 A 7/1989 Summers
4,890,611 A 1/1990 Monfort et al.
4,926,858 A 5/1990 Gifford, III et al.
4,936,845 A 6/1990 Stevens
4,986,807 A 1/1991 Farr
5,024,565 A 6/1991 Pinand
5,079,963 A 1/1992 Yamamoto et al.
5,087,265 A 2/1992 Summers
5,158,564 A 10/1992 Schnepp-Pesch et al.
5,195,954 A 3/1993 Scnepp-Pesch et al.
5,217,474 A 6/1993 Zacca et al.
5,251,120 A 10/1993 Smith
5,376,100 A 12/1994 Lefebvre
5,498,258 A 3/1996 Hakky et al.
5,527,326 A 6/1996 Hermann et al.
5,591,187 A 1/1997 Dekel
5,674,235 A 10/1997 Parisi
5,766,191 A 6/1998 Trerotola
5,787,953 A 8/1998 Jacobson
5,843,103 A 12/1998 Wulfman
5,855,586 A 1/1999 Habara et al.
5,911,722 A 6/1999 Adler et al.
5,988,006 A 11/1999 Fleytman
6,001,112 A 12/1999 Taylor
6,015,381 A 1/2000 Ouchi
6,068,603 A 5/2000 Suzuki
6,090,118 A 7/2000 McGuckin, Jr.
6,156,046 A 12/2000 Passafaro et al.
6,217,595 B1 4/2001 Shturman et al.
6,251,120 B1 6/2001 Dorn
6,258,101 B1 7/2001 Blake, III
6,270,508 B1 8/2001 Klieman et al.
6,352,539 B1 3/2002 Avellanet
6,454,779 B1 9/2002 Taylor
6,602,262 B2 8/2003 Griego et al.
6,602,264 B1 8/2003 McGuckin, Jr.
6,685,722 B1 2/2004 Rosenbluth et al.
6,824,550 B1 11/2004 Noriega et al.
6,926,725 B2 8/2005 Cooke et al.
6,997,926 B2 2/2006 Gellman et al.
7,037,316 B2 5/2006 McGuckin, Jr. et al.
7,041,116 B2 5/2006 Goto et al.
7,101,378 B2 9/2006 Salameh et al.
7,179,269 B2 2/2007 Welch et al.
7,236,203 B1 6/2007 Hojabri
7,276,067 B2 10/2007 Bales et al.
D556,527 S 12/2007 Russo et al.
7,326,203 B2 2/2008 Papineau et al.
7,357,287 B2 4/2008 Shelton, IV et al.
7,507,246 B2 3/2009 McGuckin et al.
7,559,934 B2 7/2009 Teague et al.
7,575,585 B2 8/2009 Goto et al.
7,621,923 B2 11/2009 Goldenberg
7,722,613 B2 5/2010 Sutterlin et al.
7,753,919 B2 7/2010 Kanamaru
7,819,887 B2 10/2010 McGuckin, Jr. et al.
7,822,458 B2 10/2010 Webster, III et al.
7,938,851 B2 5/2011 Olson et al.
7,946,198 B2 5/2011 Gui et al.
8,043,303 B2 10/2011 Razvi et al.
8,062,317 B2 11/2011 McGuckin, Jr. et al.
8,125,097 B1 2/2012 Lomerson, Sr. et al.
8,251,119 B2 8/2012 Toti et al.
8,298,257 B2 10/2012 Sepetka et al.
8,414,543 B2 4/2013 McGuckin, Jr. et al.
8,845,621 B2 9/2014 Fojtik
9,107,691 B2 8/2015 Fojtik
9,199,359 B2 12/2015 Marks

(56) References Cited

U.S. PATENT DOCUMENTS 10,352,411 B2 7/2019 Fojtik
10,376,278 B2 8/2019 Fojtik et al.
10,470,793 B2 11/2019 McArthur et al.
10,667,836 B2 6/2020 Fojtik et al.
11,000,307 B2 5/2021 Fojtik
11,002,346 B2 5/2021 Fojtik
2001/0041899 A1 11/2001 Foster
2002/0069715 A1 6/2002 Genco
2002/0117534 A1 8/2002 Green et al.
2003/0216760 A1 11/2003 Welch et al.
2004/0064136 A1 4/2004 Papineau et al.
2004/0172018 A1 9/2004 Okada
2005/0119615 A1 6/2005 Noriega et al.
2005/0143653 A1 6/2005 Fukuda
2005/0143768 A1 6/2005 Shiber
2005/0267323 A1 12/2005 Dorros et al.
2005/0273147 A1 12/2005 Israel
2006/0106407 A1 5/2006 McGuckin et al.
2006/0206128 A1 9/2006 Conquergood et al.
2006/0247607 A1 11/2006 Cornelius et al.
2007/0032808 A1 2/2007 Anwar et al.
2007/0149893 A1 6/2007 Heske et al.
2007/0213634 A1 9/2007 Teague
2007/0265633 A1 11/2007 Moon et al.
2007/0282303 A1 12/2007 Nash et al.
2008/0009876 A1 1/2008 Sankaran et al.
2008/0033467 A1 2/2008 Miyamoto et al.
2008/0097298 A1 4/2008 Fisher et al.
2008/0097402 A1 4/2008 Hoganson et al.
2008/0097465 A1 4/2008 Rollins et al.
2008/0103504 A1 5/2008 Schmitz et al.
2008/0277445 A1 11/2008 Zergiebel et al.
2008/0300574 A1 12/2008 Belson et al.
2009/0112255 A1 4/2009 Leopold et al.
2009/0270862 A1 10/2009 Arcenio
2009/0270893 A1 10/2009 Arcenio
2009/0275970 A1 11/2009 Leibowitz
2010/0249773 A1 9/2010 Clark et al.
2011/0024145 A1* 2/2011 Click ................. A61B 17/8827
173/2
2011/0152920 A1 6/2011 Eckhouse et al.
2011/0282370 A1 11/2011 Levine et al.
2012/0095447 A1 4/2012 Fojtik
2012/0191119 A1 7/2012 Hedstrom et al.
2012/0238905 A1 9/2012 Heske et al.
2012/0239008 A1* 9/2012 Fojtik .................. A61M 25/09
606/1
2012/0239064 A1 9/2012 Cartier et al.
2012/0253186 A1 10/2012 Simpson et al.
2013/0317529 A1 11/2013 Golden et al.
2015/0305765 A1 10/2015 Fojtik et al.
2017/0056101 A1* 3/2017 Eubanks ............ A61B 17/2909

FOREIGN PATENT DOCUMENTS

JP 2007301392 A 11/2007
JP 2007325925 A 12/2007
JP 2008520351 A 6/2008
JP 2008272488 A 11/2008
JP 2010503479 A 2/2010
JP 2015535195 A 12/2015
RO 117079 B1 10/2001
WO 9611638 A1 4/1996
WO 9717027 A1 5/1997
WO 2008033983 A1 3/2008
WO 2010115134 A1 10/2010
WO 2014074955 A1 5/2014

OTHER PUBLICATIONS

Wentzell, “Machine Design, Power Screws and Ball Screws,” Thomson Delmar Learning, (obtained from http:// www.uni.edu/~rao/MD-18%20Power%20screws.pdf. on Dec, 6, 2013). 2004.

Nagyszalanczy, “The Art of Fine Tools,” The Taunton Press, 2000

BCMA Medical Museum, 993.1220.1: Bone Drill 1914-1930, Feb. 9, 2009 (obtained from http://web.archive.org/web/20090209060158/http://bcmamedicalmuseum.org/object/993.1220.1).

Eggert, Chapter 13: Power Screws, “Engineering Design,” McGraw-Hill, 2004.

U.S. Patent and Trademark Office “International Search Report” issued in corresponding PCT/US2011/056892, Jan. 30, 2012.

U.S. Patent and Trademark Office as the International Searching Authority, “International Search Report and Written Opinion,” mailed Apr. 4, 2014, in corresponding PCT application PCT/US2013/069350.

The Crystal Reference Encyclopedia, Nitinol, 2005.

European Patent Office, “Supplementary European Search Report,” dated Jul. 18, 2014, in corresponding European Application No. 11836879.4.

International Search Report and Written Opinion dated Dec. 22, 2017 for International Application No. PCT/US2017/054871.

* cited by examiner 100
178
134
172
170
152
C
162
130
164
150
154
D
110
160
180
194
190
196
192
A
120
180
142
140
B
132
144

HANDLE ASSEMBLY FOR TISSUE RESECTION DEVICE

CROSS REFERENCE TO RELATED APPLICATIONS

This application claims the benefit of U.S. Provisional Patent Application Ser. No. 63/304,940 filed on Jan. 31, 2022, the disclosure of which is incorporated herein by reference.

TECHNICAL FIELD

The present disclosure relates generally to tissue resection devices. More particularly, the present disclosure relates to handle assemblies for tissue resection devices.

BACKGROUND

Tissue resection is a process by which undesirable growths, such as benign tumors, polyps, and fibroids are removed from within a patient's body. Removal of benign tumors, polyps, and fibroids from a female's uterus may be conducted in conjunction with a hysteroscope, which enables the physician to visualize the inside of the uterus. Small tissue resection devices have been used in conjunction with hysteroscopes to remove relatively small uterine polyps (e.g., polyps with diameters of about 3 cm or less, etc.) and fibroids (which typically have diameters of about 1 cm to about 2 cm). Some hysteroscopes are configured to distend the uterine cavity with fluid or air. With the uterine cavity distended, a light source of the hysteroscope may illuminate the interior surfaces of the uterus, and a camera of the hysteroscope and a display associated with the camera of the hysteroscope may enable a physician to visualize features, such as polyps and fibroids, on interior surfaces of the uterus. While the physician is looking at the interior surface of the uterine wall, he or she may operate a tissue resection device in conjunction with the hysteroscope to remove any polyps or fibroids that appear on the display. Debris from the tissue resection process may be aspirated through the tissue resection device, the hysteroscope, or another device, and collected for pathology.

Tissue resection procedures may also be used to remove benign tumors, polyps, and other growths from other locations within a subject's body. As an example, tissue resection procedures may also be used to remove nasal polyps. Some tissue resection devices may be electrically driven or may utilize some other power source. Some tissue resection devices may be hand operated (i.e., manually operated with the user's hand). In some procedures, hand operated tissue resection devices may offer the physician better "feel" or control than powered resection devices, and thus may be preferred for some types of procedures. However, a hand operated device may cause fatigue and/or pain to develop in the user's hand and/or arm due to ergonomics, force requirements, etc. There is an ongoing need for alternative tissue resection devices and/or methods of use and/or manufacture of said devices.

SUMMARY

In one example, a handle assembly for a tissue resection device may comprise a handle including: an elongate tubular body defining a central longitudinal axis, and a palm grip extending from the elongate tubular body, the palm grip being configured to be engaged by a palm of a user; a trigger member extending from the elongate tubular body, the trigger member being configured to be engaged by one or more fingers of the user; and a drive mechanism disposed within the elongate tubular body, the drive mechanism being configured to move a tissue resection element extending distally from the elongate tubular body. The trigger member may be engaged with the drive mechanism such that translation of the trigger member relative to the handle actuates the drive mechanism. The trigger member may be configured to translate in a direction parallel to the central longitudinal axis between a first position and a second position.

In addition or alternatively to any example described herein, the handle assembly may further comprise a return spring disposed within the elongate tubular body, wherein the return spring biases the trigger member toward the first position.

In addition or alternatively to any example described herein, the handle assembly may further comprise a resilient member extending from the palm grip to the trigger member outside of the elongate tubular body.

In addition or alternatively to any example described herein, the resilient member is configured to bias the trigger member toward the first position.

In addition or alternatively to any example described herein, the trigger member is nonpivoting relative to the elongate tubular body.

In addition or alternatively to any example described herein, the trigger member is nonpivoting relative to the palm grip.

In addition or alternatively to any example described herein, the palm grip extends radially from the central longitudinal axis a first distance, and no other structure of the handle assembly extends radially from the central longitudinal axis more than the first distance.

In addition or alternatively to any example described herein, the drive mechanism is configured to rotate the tissue resection element.

In addition or alternatively to any example described herein, the drive mechanism is configured to axially translate the tissue resection element.

In addition or alternatively to any example described herein, the drive mechanism is configured to reciprocate the tissue resection element.

In addition or alternatively to any example described herein, a tissue resection device may comprise a handle assembly. The handle assembly includes a handle including an elongate tubular body defining a central longitudinal axis, and a palm grip extending from the elongate tubular body. The palm grip is configured to be engaged by a palm of a user. The handle assembly also includes a trigger member extending from the elongate tubular body. The trigger member is configured to be engaged by one or more fingers of the user. The handle assembly also includes a drive mechanism disposed within the elongate tubular body and a return spring disposed within the elongate tubular body. The return spring biases the trigger member toward a first position. A resilient member extends from the palm grip to the trigger member outside of the elongate tubular body. The resilient member biases the trigger member toward the first position. A tissue resection element extends distally from the elongate tubular body. The drive mechanism may be configured to move the tissue resection element relative to the handle. The trigger member may be engaged with the drive mechanism such that translation of the trigger member relative to the handle actuates the drive mechanism.

In addition or alternatively to any example described herein, the trigger member is configured to translate parallel to the central longitudinal axis between a first position and a second position.

In addition or alternatively to any example described herein, the return spring exerts a first force in a distal direction against the trigger member. The resilient member exerts a second force in the distal direction against the trigger member. The first force is within 5% of the second force.

In addition or alternatively to any example described herein, the first force is substantially equal to the second force.

In addition or alternatively to any example described herein, a handle assembly for a tissue resection device may comprise: a handle including an elongate tubular body defining a central longitudinal axis, and a palm grip extending from the elongate tubular body, the palm grip being configured to be engaged by a palm of a user; a trigger member non-pivotably coupled to the handle, the trigger member being configured to be engaged by one or more fingers of the user; a drive mechanism disposed within the elongate tubular body, the drive mechanism being configured to move a tissue resection element extending distally from the elongate tubular body; and a resilient member disposed outside of the elongate tubular body and coupled to the palm grip and the trigger member. The resilient member biases the trigger member away from the palm grip. The trigger member is engaged with the drive mechanism such that translation of the trigger member along the central longitudinal axis actuates the drive mechanism.

In addition or alternatively to any example described herein, the trigger member is configured to translate in a direction parallel to the central longitudinal axis.

In addition or alternatively to any example described herein, the handle assembly may further comprise a return spring disposed within the elongate tubular body. The return spring biases the trigger member toward the first position.

In addition or alternatively to any example described herein, the resilient member is configured to balance force exerted on the trigger member by the return spring.

In addition or alternatively to any example described herein, the drive mechanism is configured to reciprocate a tissue resection element extending distally from the elongate tubular body.

In addition or alternatively to any example described herein, the trigger member extends at an oblique angle to the central longitudinal axis and the oblique angle remains generally constant when the trigger member is translated along the central longitudinal axis.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figure 1:
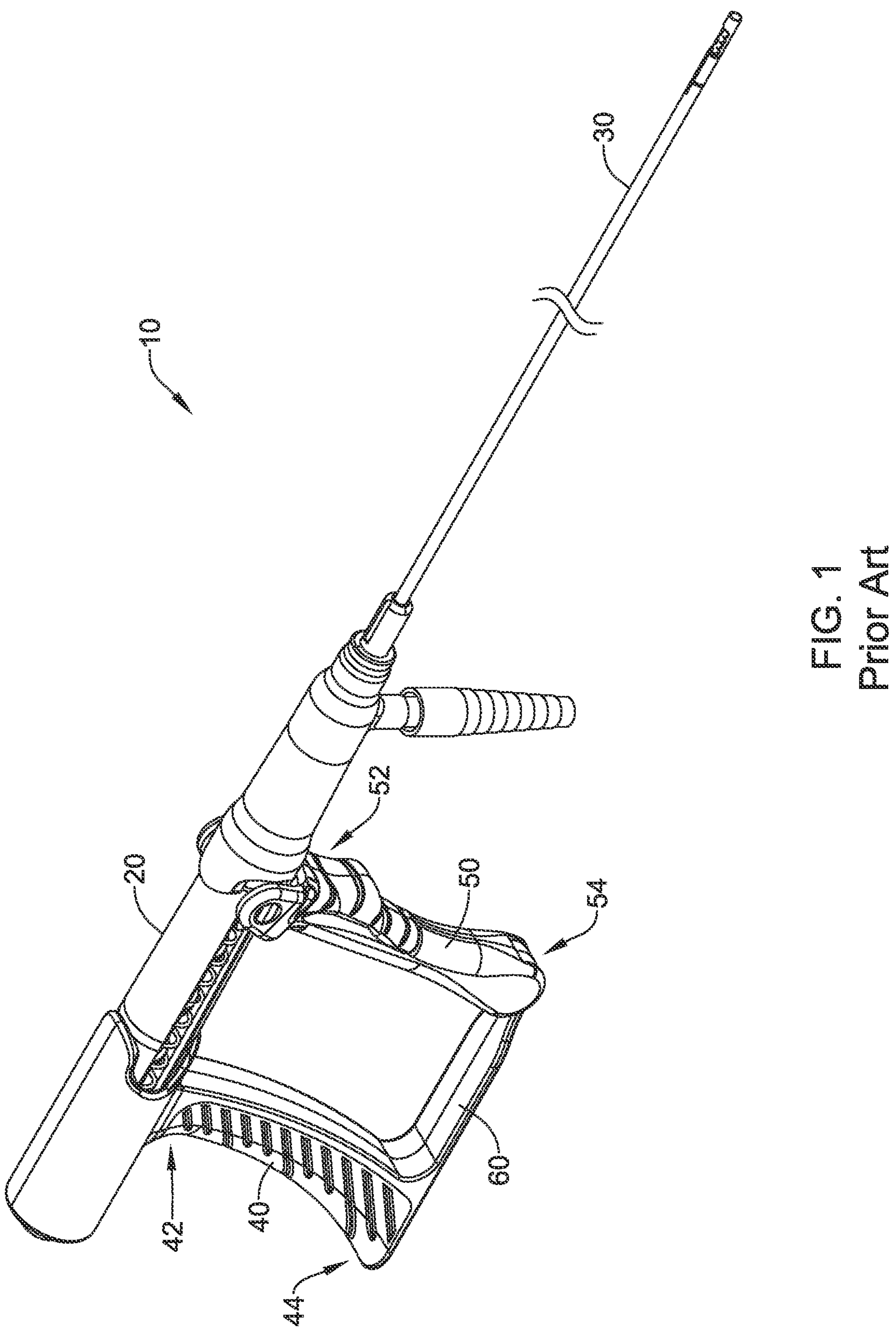
FIGS. 1-3 illustrate selected aspects of a prior art tissue resection device.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate example embodiments of the disclosure but not limit the disclosure. Those skilled in the art will recognize that the various elements described and/or shown may be arranged in various combinations and configurations without departing from the scope of the disclosure. However, in the interest of clarity and ease of understanding, every feature and/or element may not be shown in each drawing.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered the greatest possible dimension measured according to the intended usage, while a "minimum extent" may be considered the smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to some features may be equally referred to all instances and quantities beyond one of said feature(s) unless clearly stated to the contrary. As such, it will be understood that the following discussion may apply equally to any and/or all of the components for which there are more than one within the device, etc. unless explicitly stated to the contrary.

Additionally, it should be noted that in any given figure, some features may not be shown, or may be shown schematically, for clarity and/or simplicity. Additional details regarding some components and/or method steps may be illustrated in other figures in greater detail. The devices and/or methods disclosed herein may provide a number of desirable features and benefits as described in more detail below.

Figure 2:
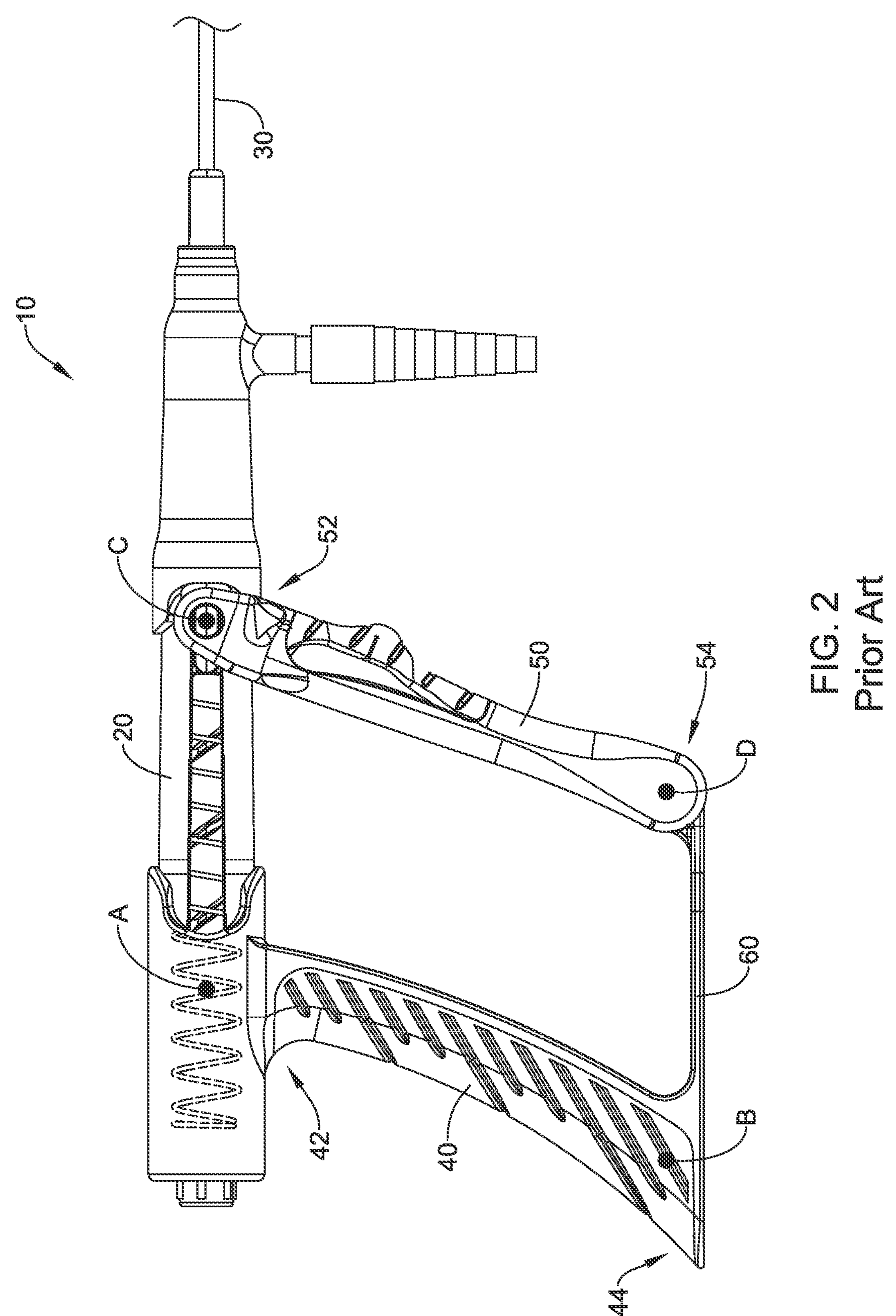
Figure 3:
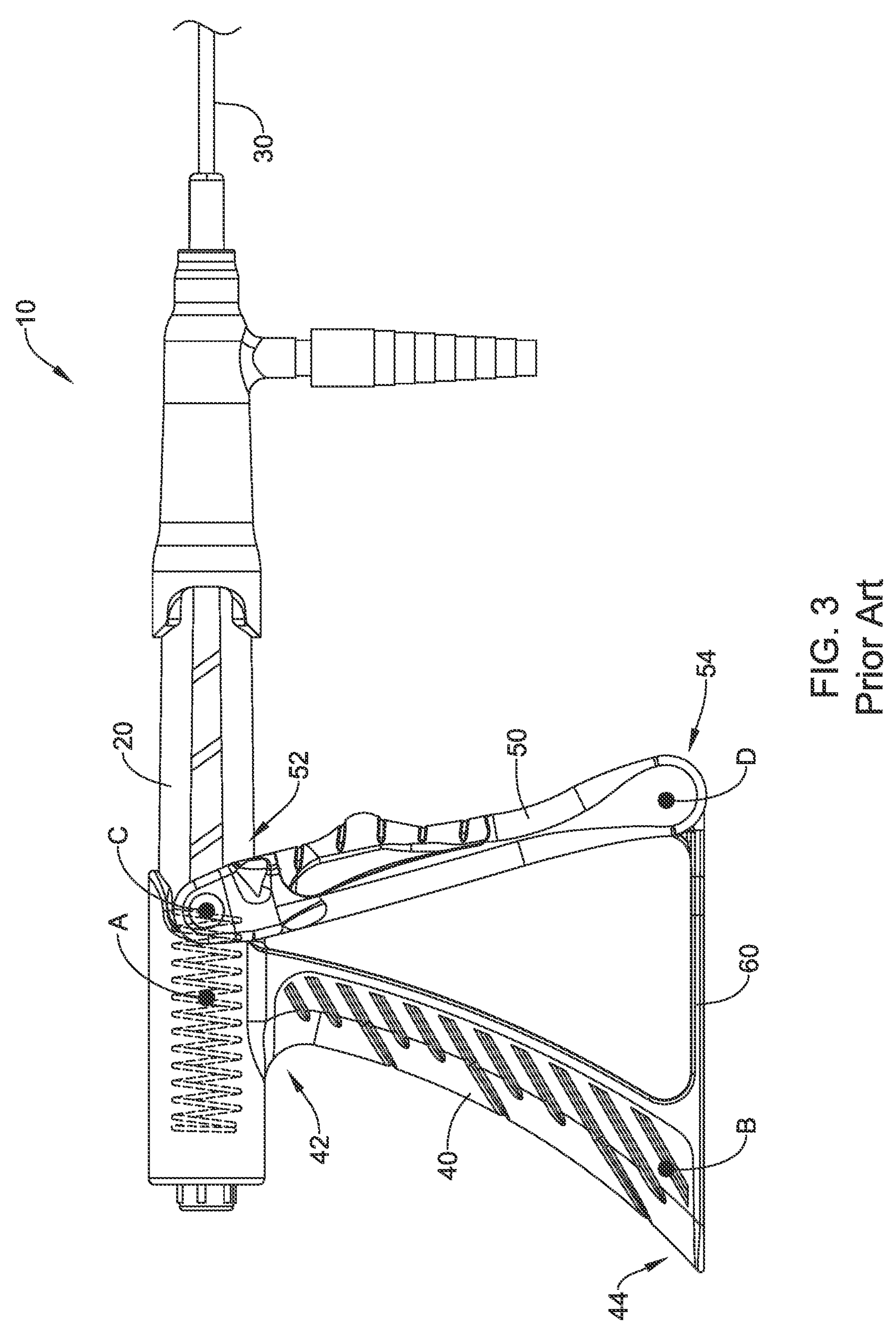

FIG. 1 is a perspective view illustrating selected aspects of a tissue resection device 10. The tissue resection device 10 includes a tubular body 20 having a drive mechanism disposed therein. The tissue resection device 10 includes an elongate shaft 30 extending distally from the tubular body 20. The tissue resection device 10 includes a grip 40 extending from the tubular body 20. The grip 40 may include a first end 42 proximate the tubular body 20 and a second end 44 opposite the first end 42. The tissue resection device 10 includes an actuator 50 pivotably coupled to the drive mechanism and/or the tubular body 20 at a first end 52. The actuator 50 may include a second end 54 opposite the first end 52. The tissue resection device 10 includes a longitudinal support member 60 extending between the second end 44 of the grip 40 and the second end 54 of the actuator 50. The longitudinal support member 60 is substantially straight and parallel to the tubular body 20. The longitudinal support member 60 has very limited flexibility and is generally rigid. The actuator 50 may be pivotably coupled to the longitudinal support member 60 at the second end 54 opposite the first end 52. The tissue resection device 10 includes a return mechanism within the tubular body 20 that urges the actuator 50 toward an initial configuration (e.g., distalmost position), shown in FIG. 2. The tissue resection device 10 includes a resection element engaged with the drive mechanism to resect tissue proximate a distal end of the elongate shaft. The tissue resection device 10 includes a suction port for aspiration of the resected tissue through the elongate shaft 30. Operation of the actuator 50, illustrated in FIGS. 2-3, involves longitudinal movement of the first end 52 of the actuator 50 toward the grip 40 to a second position (e.g., proximalmost position) while the second end 54 of the actuator 50 pivots around a pivot point where the actuator 50 is pivotably coupled to the longitudinal support member 60. The longitudinal support member 60 prevents the second end 54 of the actuator 50 from moving longitudinally toward the grip 40. In order to help clarify the movements, reference points A, B, C, and D are shown on FIGS. 2 and 3.

The construction of the actuator 50 described herein largely limits force applied to the actuator 50 to that exerted by a user's index finger and middle finger, which would be positioned near the first end 52 of the actuator 50. Fingers positioned adjacent the second end 54 of the actuator 50 may have less force transferred to the actuator 50 due to the pivoting motion instead of longitudinal motion, and thus have less effect on operation of the actuator 50. While generally effective at actuating the drive mechanism, in some cases, this operation may lead to fatigue and/or stress in the user's index and middle fingers, as well as the hand and wrist/forearm.

Figure 4:
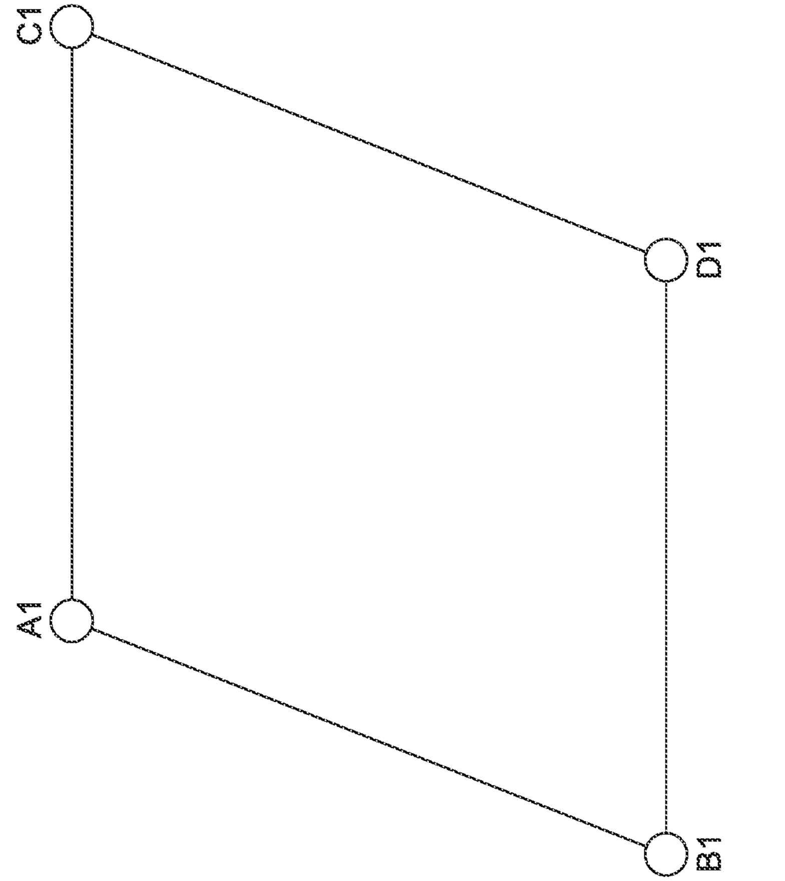
FIGS. 4-5 schematically illustrate how the relative positioning of selected features of the prior art tissue resection device changes during use.
Figure 5:
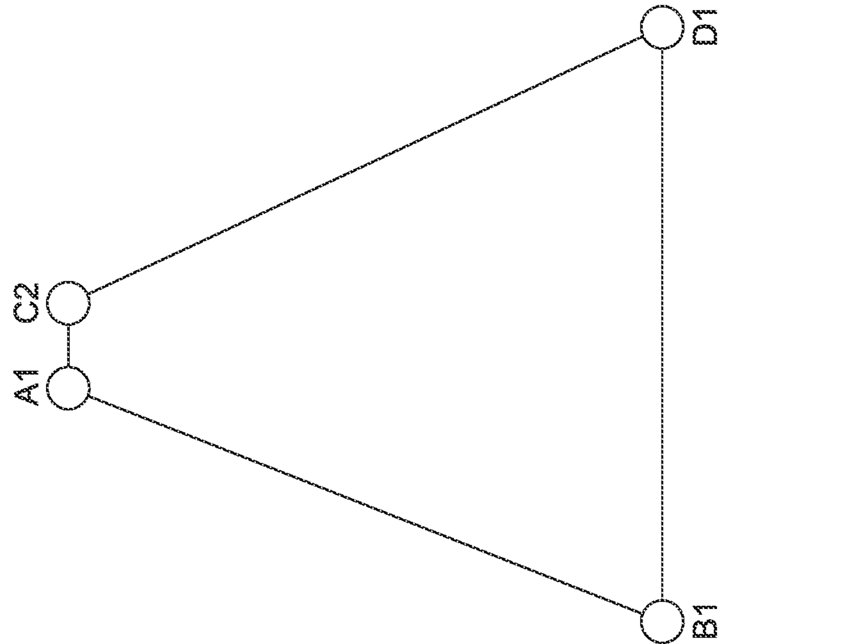

FIGS. 4 and 5 schematically illustrate how the reference points A, B, C, and D on the tissue resection device 10 move during operation of the actuator 50. In an initial configuration of the actuator 50, the first end 42 (e.g., FIGS. 1-2) of the grip 40 may be located at position A1 and the second end 44 (e.g., FIGS. 1-2) of the grip 40 may be located at position B1, and the first end 52 (e.g., FIGS. 1-2) of the actuator 50 may be located at position C1 and the second end 54 (e.g., FIGS. 1-2) of the actuator 50 may be located at position D1, as shown in FIG. 4. During operation, the first end 52 (e.g., FIGS. 1-2) of the actuator 50 may be moved longitudinally toward the grip 40 and/or the second configuration, such that the first end 52 (e.g., FIGS. 1-2) of the actuator 50 moves from position C1, shown in FIG. 4, to position C2, as seen in FIG. 5. As shown in FIG. 5, the second end 54 (e.g., FIGS. 1-2) of the actuator 50 remains at position D1 in the second configuration of the actuator 50.

Figure 6:
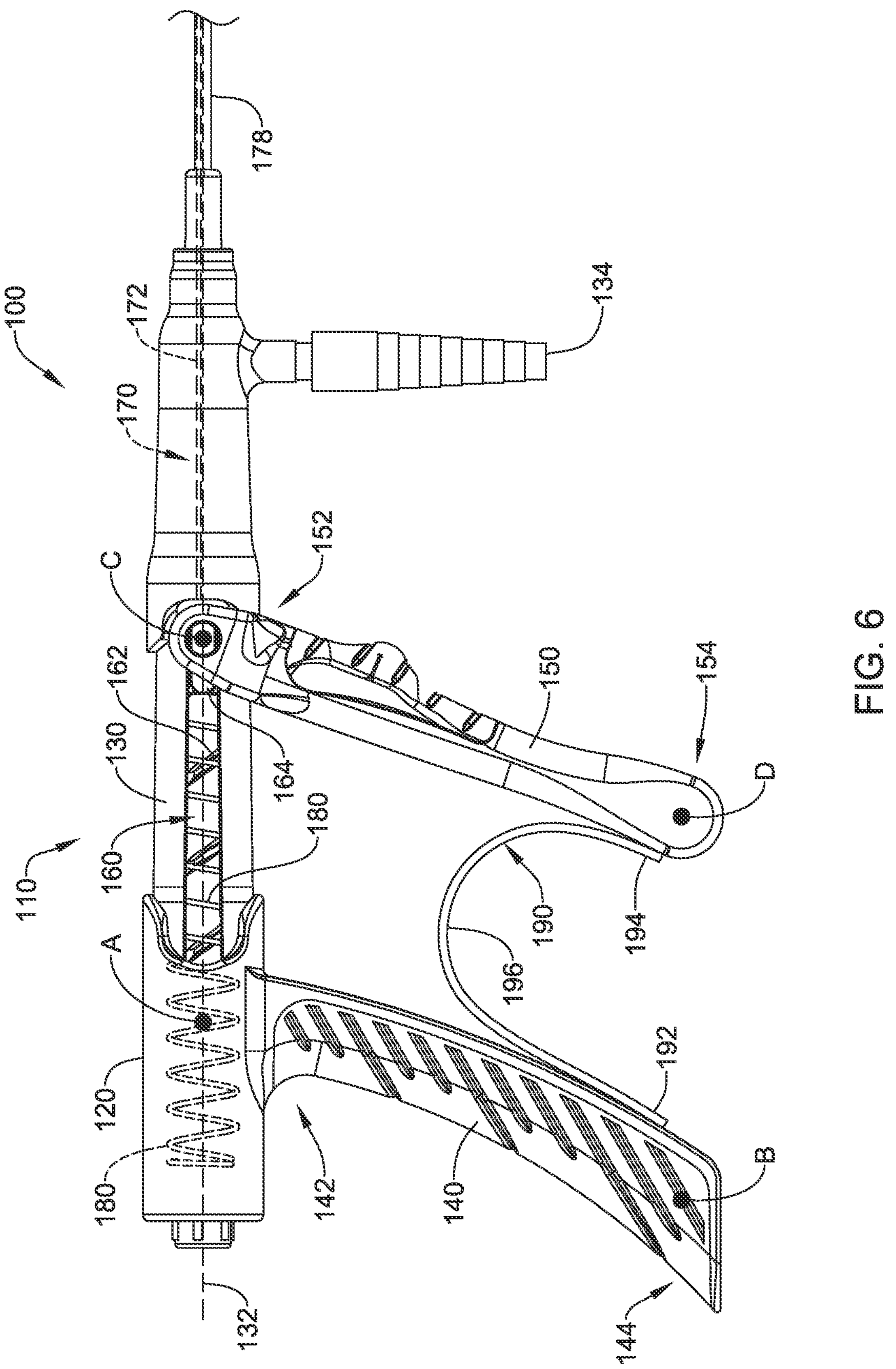
FIGS. 6-7 illustrate selected aspects of a tissue resection device according to the disclosure.
Figure 7:
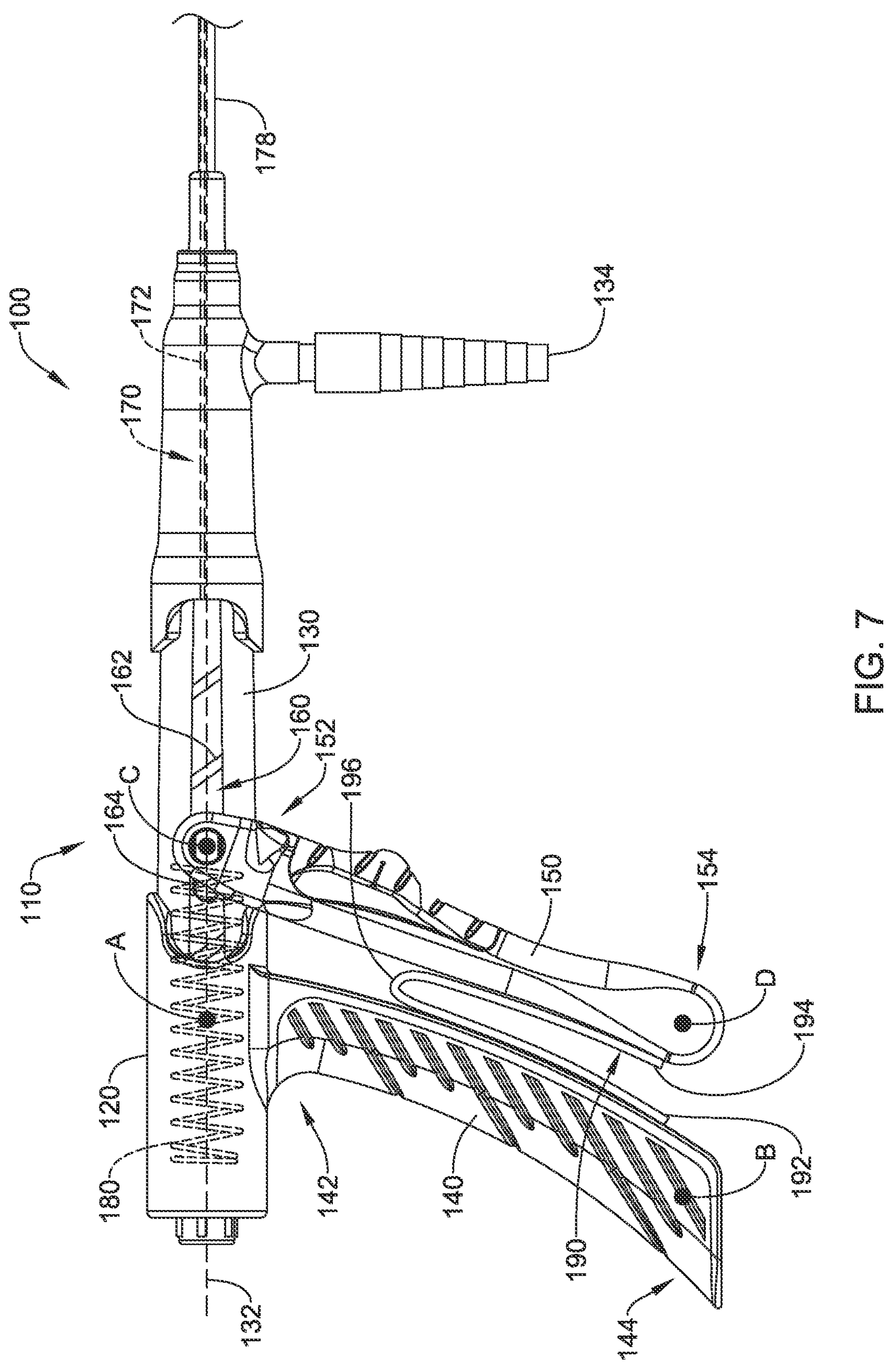

FIGS. 6-7 illustrate a tissue resection device 100 according to the disclosure. In some embodiments, the tissue resection device 100 may include a handle assembly 110. In some embodiments, the tissue resection device 100 and/or the handle assembly 110 may comprise a handle 120 including an elongate tubular body 130 defining a central longitudinal axis 132 and a palm grip 140 extending from the elongate tubular body 130. The palm grip 140 may include a first end 142 proximate the elongate tubular body 130 and a second end 144 opposite the first end 142. The palm grip 140 may be configured to be engaged by and/or contacted by a palm and/or a hand of a user. In at least some embodiments, when the palm grip 140 is engaged by the palm and/or the hand of the user, a thumb of the user may extend toward a distal end of the handle assembly 110 and/or the tissue resection device 100 along a first side of the palm grip 140 and fingers of the user may extend toward the distal end of the handle assembly 110 and/or the tissue resection device 100 along a second side of the palm grip 140 opposite the first side of the palm grip 140.

The tissue resection device 100 and/or the handle assembly 110 may include a trigger member 150 extending from the elongate tubular body 130. The trigger member 150 may include a first end 152 proximate the elongate tubular body 130 and a second end 154 opposite the first end 152. The trigger member 150 may be configured to be engaged by one or more fingers of the user. In some embodiments, the trigger member 150 may be oriented generally parallel to the palm grip 140. In some embodiments, the trigger member 150 and/or the first end 152 of the trigger member 150 may be slidingly engaged with and/or slidingly coupled to the elongate tubular body 130. Some suitable but non-limiting examples of materials that may be used to form the handle assembly 110, the handle 120, the elongate tubular body 130, the palm grip 140, and/or the trigger member 150, including but not limited to polymers, metals, composites, and the like, are described below.

In some embodiments, the tissue resection device 100 and/or the handle assembly 110 may include a drive mechanism 160 disposed within the elongate tubular body 130. The drive mechanism 160 may be configured to move a tissue resection element 170 extending distally from the elongate tubular body 130. In some embodiments, the tissue resection element 170 may include a drive shaft 172 extending distally from the handle assembly 110, the handle 120, and/or the elongate tubular body 130. In some embodiments, the tissue resection element 170 may include a resection member (not shown) coupled to, disposed at, and/or fixedly attached to a distal end of the drive shaft 172. The resection member may be configured to resect tissue proximate a distal end of the tissue resection device 100. In some embodiments, the drive shaft 172 may be substantially rigid. In some embodiments, the drive shaft 172 may be flexible to facilitate bending and/or curvature of the tissue resection device 100. In some embodiments, the drive shaft 172 may comprise a wire of a known type and configuration. In some embodiments, the drive shaft 172 may comprise or consist of a solid filament. Alternatively, in some embodiments, the drive shaft 172 may include a coiled filament, which may surround a solid filament. In some embodiments, the drive shaft 172 may have any of a variety of suitable cross-sectional shapes; for example, round (e.g., circular, elliptical, oval, etc.), polygonal (e.g., triangular, rectangular, hexagonal, etc.), a flattened shape, or the like. Optionally, the drive shaft 172 may include features that facilitate engagement and/or cutting of tissue, such as grooves or teeth that engage tissue or teeth or a sharpened edge that cuts into tissue.

In some embodiments, the tissue resection device 100 may include an elongate sheath 178 extending distally from the handle assembly 110. In some embodiments, the drive shaft 172 may extend distally within the elongate sheath 178 to protect the drive shaft 172 during operation and/or to protect the patient's anatomy from movement of the drive shaft 172 during operation. In some embodiments, the resection member may be disposed at a distal end of the elongate sheath 178. In some embodiments, the resection member may extend distally from the distal end of the elongate sheath 178.

In some embodiments, the elongate sheath 178 may have an outer diameter of about 5 French (e.g., 0.066 inch; 1.67 millimeters), about 7 French (e.g., 0.092 inch; 2.33 millimeters) or about 9 French (e.g., 0.118 inch; 3 millimeters), which may correspond to the size of a hysteroscope (e.g., to the size of an access lumen through the hysteroscope, etc.) with which the tissue resection device 100 is to be used. The elongate sheath 178 may have any suitable length. In some embodiments, the elongate sheath 178 of the tissue resection device 100 may be about 35 centimeters long (e.g., about 33-37 centimeters long, about 30-40 centimeters long, etc.) or another suitable (e.g., shorter or longer) length.

In some embodiments, at or near its distal end, the elongate sheath 178 may include an opening through an outer wall of the elongate sheath 178 configured to receive tissue (e.g., soft tissue, undesirable growths, such as uterine polyps and fibroids, soft tissue to be biopsied, a tumor, a portion of a ligament, a tendon, or a bone, etc.). In some embodiments, the edges of the outer wall that define the opening may be configured to facilitate separation of the tissue that is to be removed (e.g., unwanted tissue, etc.) from adjacent tissue (e.g., healthy tissue, etc.). A size of the opening may depend on a particular use for which the tissue resection device 100 is configured. Without limitation, the opening may have a length of about 5 mm, a length of about 7.5 mm or any other suitable length. In some embodiments, the resection member may be disposed proximal of the distal end of the elongate sheath 178 at and/or proximate the opening in the outer wall of the elongate sheath 178.

In some embodiments, the elongate tubular body 130 may include an outflow port 134. In some embodiments, the outflow port 134 may be integrally formed and/or monolithically formed with the elongate tubular body 130. In some embodiments, the outflow port 134 may be in fluid communication with the lumen of the elongate sheath 178. In some embodiments, the outflow port 134 may be integrally formed and/or monolithically formed with the elongate sheath 178. Other configurations are also contemplated. In some embodiments, the outflow port 134 may be configured to connect to a suction source (not shown) to facilitate aspiration through the lumen of the elongate sheath 178 during operation of the tissue resection device 100. In some embodiments, suction may draw tissue and/or may help to draw tissue to be resected into and/or through the opening in the outer wall of the elongate sheath 178.

The tissue resection element 170 and/or the elongate sheath 178 may be of any suitable size (e.g., have an outer diameter) that will cut tissue in the desired manner while enabling the tissue to be aspirated through the lumen of the elongate sheath 178 at an acceptable rate (e.g., at a rate that will minimize the duration of a tissue resection procedure and, thus, the pain suffered by a patient, etc.). As an example, acceptable rates of aspiration may be achieved with a lumen having an open cross-sectional area (e.g., the cross-sectional area of the lumen of the elongate sheath 178 minus the cross-sectional area of the tissue resection element 170 and/or the drive shaft 172) that is at least 50% of the cross-sectional area of the elongate sheath 178. In some embodiments, the use of smaller drive shafts could provide a larger percentage of open cross-sectional area (e.g., at least 60%, at least 65%, at least 70%, etc.) and enable greater rates of aspiration.

In some embodiments, the drive shaft 172 may include features (e.g., helical grooves, teeth, a helical thread, etc.) that facilitate the proximal movement of tissues through the lumen of the elongate sheath 178, for example, by breaking down tissues and other materials as they move proximally through the lumen, by forcing larger pieces proximally through the lumen, or by any other suitable mechanism.

Some suitable but non-limiting examples of materials that may be used to form the drive mechanism 160, the tissue resection element 170, the drive shaft 172, the elongate sheath 178, the resection member, etc., including but not limited to polymers, metals, composites, and the like, are described below.

The drive mechanism 160 may be configured to move the tissue resection element 170, the drive shaft 172, and/or the resection member relative to the handle 120, the elongate tubular body 130, and/or the elongate sheath 178. In some embodiments, the drive mechanism 160 may be configured to rotate the tissue resection element 170, the drive shaft 172, and/or the resection member relative to the elongate tubular body 130 and/or the elongate sheath 178. In some embodiments, the drive mechanism 160 may be configured to longitudinally translate the tissue resection element 170, the drive shaft 172, and/or the resection member relative to the elongate tubular body 130 and/or the elongate sheath 178. In some embodiments, the drive mechanism 160 may be configured to reciprocate the tissue resection element 170, the drive shaft 172, and/or the resection member relative to the elongate tubular body 130 and/or the elongate sheath 178. In some embodiments, the drive mechanism 160 may be configured to rotationally oscillate (e.g., rotate back-and-forth in clockwise and counter-clockwise directions) the tissue resection element 170, the drive shaft 172, and/or the resection member relative to the elongate tubular body 130 and/or the elongate sheath 178. In some embodiments, the drive mechanism 160 may be configured to axially reciprocate the tissue resection element 170, the drive shaft 172, and/or the resection member relative to the elongate tubular body 130 and/or the elongate sheath 178. Other configurations are also contemplated.

In some embodiments, the drive mechanism 160 may include a generally cylindrical shaft having a helical thread 162 formed thereon and/or therein. In some embodiments, the drive mechanism 160 may include a slider 164 coupled to and/or engaged with the trigger member 150. In some embodiments, the slider 164 may be engaged with the helical thread 162 and configured to slide relative to the elongate tubular body 130. Accordingly, in at least some embodiments, the trigger member 150 and/or the first end 152 of the trigger member 150 may be engaged with the drive mechanism 160 such that translation of the trigger member 150 relative to the handle 120 and/or the elongate tubular body 130 actuates the drive mechanism 160. In some embodiments, translation of the trigger member 150 relative to the handle 120 and/or the elongate tubular body 130 may translate the slider 164 longitudinally along the generally cylindrical shaft and/or the helical thread 162. Relative motion between the slider 164 and the helical thread 162 may cause and/or force the generally cylindrical shaft to rotate within and/or relative to the elongate tubular body 130.

In some embodiments, the trigger member 150 may be configured to translate axially along the central longitudinal axis 132 between a first position (e.g., FIG. 6), which may be a distalmost position, and a second position (e.g., FIG. 7), which may be a proximalmost position. In some embodiments, the trigger member 150 may be configured to translate in a direction parallel to the central longitudinal axis 132 between the first position and the second position. In other words, both the first end 152 and the opposite second end 154 of the trigger member 150 may move proximally and distally the same amount in a direction that is parallel to the central longitudinal axis 132 between the first position (e.g., the distalmost position) and the second position (e.g., the proximalmost position) to actuate the drive mechanism 160 to thereby move (e.g., rotate, translate, etc.) the drive shaft 172 and associated tissue resection member relative to the elongate sheath 178. The trigger member 150 may be engaged with the drive mechanism 160 such that translation of the trigger member 150 along the central longitudinal axis 132 actuates the drive mechanism 160 to move the tissue resection element 170, the drive shaft 172, and/or the resection member. The trigger member 150 may be engaged with the drive mechanism 160 such that translation of the trigger member 150 axially and/or longitudinally relative to the handle 120 and/or the elongate tubular body 130 actuates the drive mechanism 160 to move (e.g., rotate, translate, etc.) the tissue resection element 170, the drive shaft 172, and/or the resection member.

In at least some embodiments, the trigger member 150 may be nonpivoting relative to the handle 120. In some embodiments, the trigger member 150 may be nonpivoting relative to the elongate tubular body 130. In some embodiments, the trigger member 150 may be nonpivoting relative to the palm grip 140. In some embodiments, the trigger member 150 may be nonpivoting relative to the central longitudinal axis 132. In some embodiments, the trigger member 150 may be nonpivoting relative to the drive mechanism 160 and/or the slider 164 of the drive mechanism 160.

In some embodiments, the trigger member 150 may extend radially and/or laterally from the elongate tubular body 130 and/or the central longitudinal axis 132 toward the second end 154 of the trigger member 150. In some embodiments, the first end 152 of the trigger member 150 may be fixedly secured to the slider 164 of the drive mechanism 160. In some embodiments, the trigger member 150 may be nonpivotably attached to the slider 164 of the drive mechanism 160. In some embodiments, the slider 164 may include pins extending from opposite sides of the slider 164 to engage the trigger member 150. In some embodiments, the trigger member 150 may be pinned and/or may include a cross-shaft (e.g., a pin) oriented perpendicular to the central longitudinal axis 132. In some embodiments, a central axis of the cross-shaft may be oriented perpendicular to and/or may translate along the central longitudinal axis 132. In at least some embodiments, the central axis of the cross-shaft may intersect the central longitudinal axis 132. In some embodiments, the cross-shaft may move and/or axially translate along the central longitudinal axis 132 during operation and/or movement of the trigger member 150 relative to the elongate tubular body 130. In at least some embodiments, the cross-shaft may engage with the slider 164. In some embodiments, the cross-shaft may be fixedly attached to the slider 164. In some embodiments, the cross-shaft may include two half cross-shafts (e.g., first and second pins) disposed on opposite sides of the generally cylindrical shaft. In some embodiments, the cross-shaft does not extend through the generally cylindrical shaft. In some embodiments, the cross-shaft does not extend completely through the elongate tubular body 130. In some embodiments, the cross-shaft does not extend into the elongate tubular body 130 at all. In some embodiments, the cross-shaft engages and/or is fixedly attached to the slider 164 outside of the elongate tubular body 130 and the slider 164 extends into the elongate tubular body 130 to engage the helical thread 162 on the generally cylindrical shaft. Other configurations are also contemplated.

In some embodiments, the trigger member 150 may extend radially and/or laterally from the elongate tubular body 130 and/or the central longitudinal axis 132 at an oblique angle to the handle 120 and the central longitudinal axis 132. In some embodiments, the trigger member 150 may extend radially and/or laterally from the elongate tubular body 130 and/or the central longitudinal axis 132 at an oblique angle to the elongate tubular body 130 and the central longitudinal axis 132. In some embodiments, the trigger member 150 may extend radially and/or laterally from the elongate tubular body 130 and/or the central longitudinal axis 132 at an oblique angle to the central longitudinal axis 132. In some embodiments, the oblique angle may remain generally constant when the trigger member 150 is translated along the central longitudinal axis 132 between the first position (e.g., the distalmost position) and the second position (e.g., the proximalmost position). In some embodiments, the oblique angle may remain generally constant when the trigger member 150 is translated axially and/or longitudinally relative to the handle 120 and/or the elongate tubular body 130 in a direction parallel to the central longitudinal axis 132 between the first position (e.g., the distalmost position) and the second position (e.g., the proximalmost position).

In some embodiments, the palm grip 140 extends radially and/or laterally from the elongate tubular body 130 and/or the central longitudinal axis 132 toward the second end 144 of the palm grip 140 at an oblique angle to the elongate tubular body 130 and/or the central longitudinal axis 132. In some embodiments, the palm grip 140 extends radially and/or laterally from the elongate tubular body 130 and/or the central longitudinal axis 132 toward the second end 144 of the palm grip 140 at an oblique angle to the elongate tubular body 130 and/or the central longitudinal axis 132 a first distance from the central longitudinal axis 132. In at least some embodiments, the first distance may be measured perpendicular and/or normal to the central longitudinal axis 132. In some embodiments, the first distance may be measured along an axis of the palm grip 140 from the first end 142 to the second end 144 at an oblique angle to the central longitudinal axis. In some embodiments, no other structure of the handle assembly 110 and/or the handle 120 extends radially and/or laterally from the central longitudinal axis 132 more than the first distance. As such, in some embodiments, the palm grip 140 and/or the second end 144 of the palm grip 140 may form and/or define an outermost extent of the tissue resection device 100, the handle assembly 110, and/or the handle 120. The outermost extent may be defined radially and/or laterally from the central longitudinal axis 132.

In some embodiments, the handle assembly 110 may include a return spring 180 disposed within the elongate tubular body 130. In at least some embodiments, the return spring 180 may be disposed about the drive mechanism 160 and/or the generally cylindrical shaft having the helical thread 162. In some embodiments, the return spring 180 may be disposed within the generally cylindrical shaft. Other configurations are also contemplated. In some embodiments, the return spring 180 may be configured to bias the trigger member 150 away from the palm grip 140. In some embodiments, the return spring 180 may be configured to bias the trigger member 150 toward the first position (e.g., the distalmost position). In at least some embodiments, the return spring 180 may be a coil spring. In some embodiments, the return spring 180 may be a compression spring and/or may be disposed within the elongate tubular body 130 in compression. In some embodiments, the return spring 180 may be a tension spring and/or may be disposed within the elongate tubular body 130 in tension. Other configurations are also contemplated. Some suitable but non-limiting examples of materials that may be used to form the return spring 180, including but not limited to polymers, metals, composites, and the like, are described below.

In some embodiments, the handle assembly 110 may include a resilient member 190 (e.g., a flexible spring) extending from the palm grip 140 to the trigger member 150 outside of the elongate tubular body 130. The resilient member 190 may include a first end 192, a second end 194 opposite the first end 192, and a body portion 196 disposed and/or extending between the first end 192 and the second end 194. In at least some embodiments, the body portion 196 may be curved, deflected, and/or bent.

In some embodiments, the resilient member 190 may be configured to bias the trigger member 150 away from the palm grip 140. In some embodiments, the resilient member

190 may be configured to bias the trigger member 150 toward the first position (e.g., the distalmost position). In at least some embodiments, the resilient member 190 may be a coil spring. In some embodiments, the resilient member 190 may be a compression spring and/or may be disposed between the palm grip 140 and the trigger member 150 in compression. In at least some embodiments, the resilient member 190 may be a flattened strip of material or leaf spring disposed between the palm grip 140 and the trigger member 150 in a flexed or bent configuration and held in flexure therebetween. In some embodiments, the resilient member 190 and/or the flattened strip of material may be coupled to and/or attached to the palm grip 140 and the trigger member 150 in a deflected, curved and/or bent configuration and held in flexure therebetween. The resilient member 190 and/or the flattened strip of material may be biased toward a straight or straighter configuration. Some suitable but non-limiting examples of materials that may be used to form the resilient member 190 including but not limited to polymers, metals, composites, and the like, are described below.

In some embodiments, the resilient member 190 (e.g., a first end 192 of the resilient member 190) may be fixedly attached to the palm grip 140. In some embodiments, the resilient member 190 (e.g., a second end 194 of the resilient member 190) may be fixedly attached to the trigger member 150. In some embodiments, the resilient member 190 may be mechanically fastened to the palm grip 140 (e.g., with screw(s), rivet(s), pin(s), hook(s) and loop(s), etc.). In some embodiments, the resilient member 190 may be mechanically fastened to the trigger member 150 (e.g., with screw(s), rivet(s), pin(s), hook(s) and loop(s), etc.). In some embodiments, the resilient member 190 may be fixedly attached to the palm grip 140 using a combination of mechanical fastening, mechanical coupling and/or adhesive bonding. In some embodiments, the resilient member 190 may be fixedly attached to the trigger member 150 using a combination of mechanical fastening, mechanical coupling and/or adhesive bonding. In some embodiments, the palm grip 140 and/or the trigger member 150 may include a notch, a recess, a groove, a protrusion, a slot, etc. configured to receive and/or abut the first end 192 and/or the second end 194, respectively, of the resilient member 190.

In some embodiments, the resilient member 190 may be integrally formed with and/or co-molded with the palm grip 140 and fixedly attached to the trigger member 150. In some embodiments, the resilient member 190 may be integrally formed with and/or co-molded with the trigger member 150 and fixedly attached to the palm grip 140. In some embodiments, the resilient member 190 may be integrally formed with and/or co-molded with the palm grip 140 and the trigger member 150. In some embodiments, the resilient member 190 may be formed as a living hinge extending between the palm grip 140 and the trigger member 150. In some embodiments, the resilient member 190 may be formed from a metallic material and the palm grip 140 and/or the trigger member 150 may be overmolded onto the resilient member 190 (e.g., the metallic material). Other configurations are also contemplated.

In some embodiments, the return spring 180 exerts and/or may be configured to exert a first force in a distal direction against the trigger member 150. In some embodiments, the resilient member 190 exerts and/or may be configured to exert a second force in a distal direction against the trigger member 150. In some embodiments, the first force may be within about 25% of the second force. In some embodiments, the first force may be within about 20% of the second force. In some embodiments, the first force may be within about 15% of the second force. In some embodiments, the first force may be within about 10% of the second force. In some embodiments, the first force may be within about 5% of the second force. In some embodiments, the first force may be substantially equal to the second force. In some embodiments, the resilient member 190 may be configured to balance force (e.g., the first force) exerted on the trigger member 150 by the return spring 180. Other configurations are also contemplated.

Figure 8:
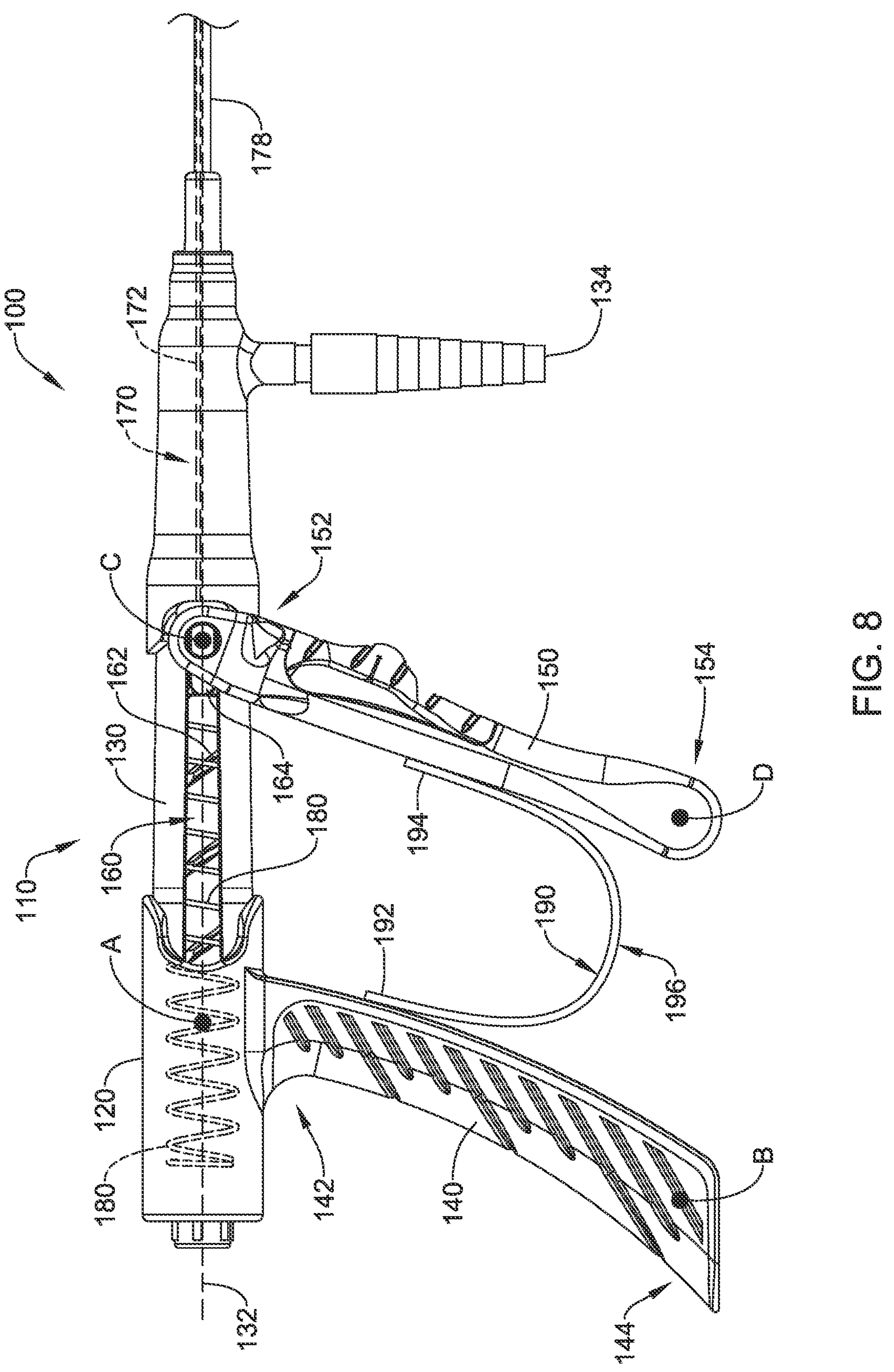
FIGS. 8-9 illustrate an alternative configuration of the tissue resection device of FIGS. 6-7.
Figure 9:
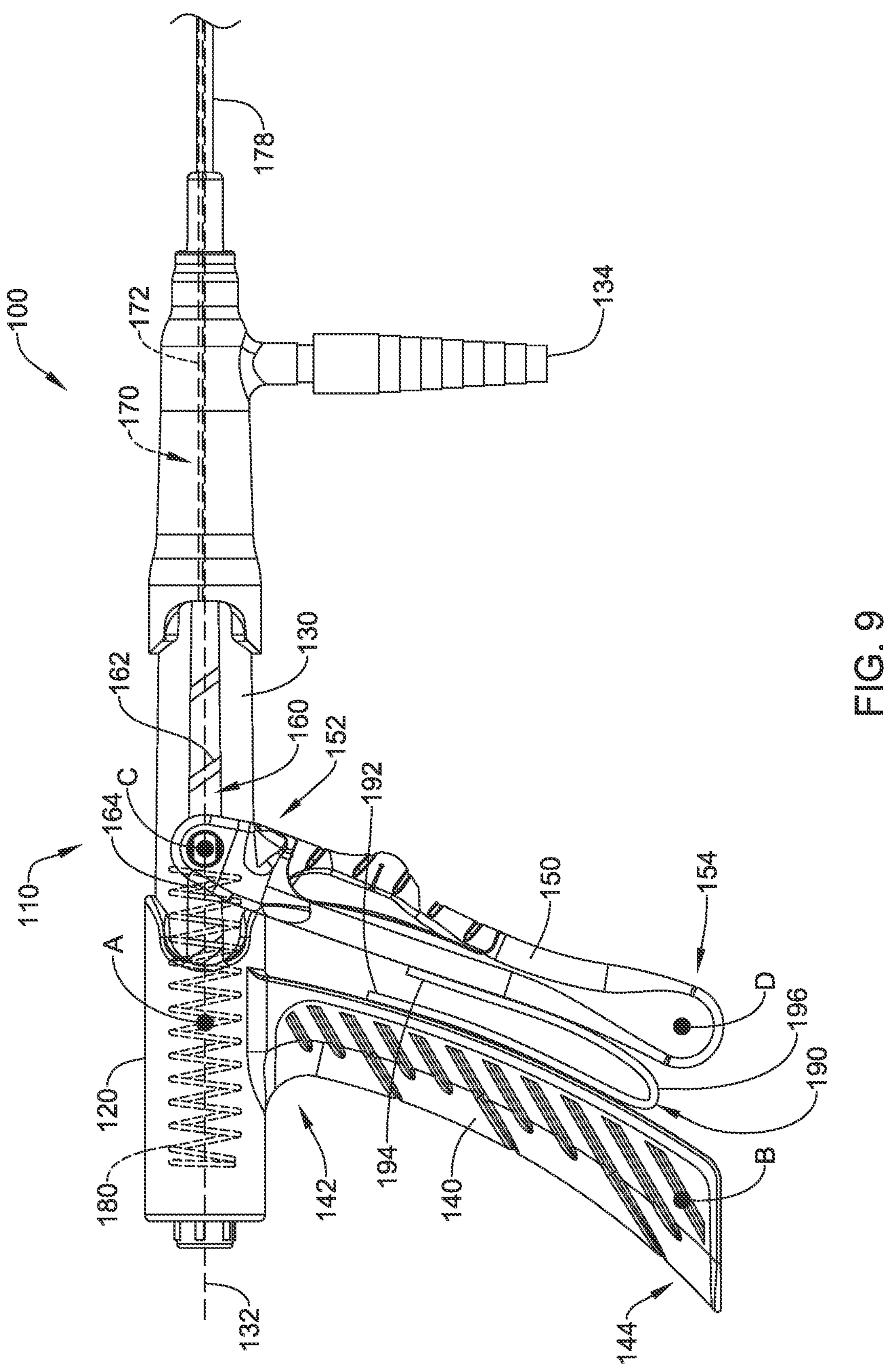

In the configuration illustrated in FIGS. 6-7, the resilient member 190 may be oriented with the first end 192 and the second end 194 disposed and/or extending away from the elongate tubular body 130 and the curved body portion 196 of the resilient member 190 oriented toward the elongate tubular body 130. In some embodiments, the first end 192 may be disposed proximate the second end 144 of the palm grip 140 and the second end 194 may be disposed proximate the second end 154 of the trigger member 150. Accordingly, the body portion 196 of the resilient member 190 may be disposed and/or positioned closer to the elongate tubular body 130 than the first end 192 and the second end 194 of the resilient member 190. In an alternative configuration, the resilient member 190 may be oriented with the first end 192 and the second end 194 disposed and/or extending toward the elongate tubular body 130 (e.g., extending toward the first end 142 of the palm grip 140 and the first end 152 of the trigger member 150, respectively) and the curved body portion 196 of the resilient member 190 oriented away from the elongate tubular body 130 (e.g., disposed between and/or extending toward the second end 144 of the palm grip 140 and the second end 154 of the trigger member 150). Accordingly, the body portion 196 of the resilient member 190 may be disposed and/or positioned farther from the elongate tubular body 130 than the first end 192 and the second end 194 of the resilient member 190, as seen in FIGS. 8-9. Other configurations are also contemplated.

The resilient member 190 may be positioned and oriented between the palm grip 140 and the trigger member 150 such that no portion of the resilient member 190 extends beyond the second end 144 of the palm grip 140 and the second end 154 of the trigger member 150. In other words, the resilient member 190 may be positioned and oriented such that the curved body portion 196 is closer to the elongate tubular body 130 than the furthest ends of the palm grip 140 and the trigger member 150 (e.g., the second end 144 of the palm grip 140 and the second end 154 of the trigger member 150) are from the elongate tubular body 130 in both the first position (e.g., the distalmost position) and the second position (e.g., the proximalmost position).

Operation of the handle assembly 110, illustrated in FIGS. 6-7 and 8-9, involves longitudinal movement of the trigger member 150 toward the palm grip 140. In order to help clarify the movements, reference points A, B, C, and D are shown in the figures.

The operation of the handle assembly 110 described herein permits force applied to the trigger member 150 to include force exerted by all of the user's fingers that are engaged with the trigger member 150. In at least some embodiments, force vectors may be distributed generally evenly along the trigger member 150. Accordingly, fingers positioned adjacent the first end 152 of the trigger member 150 and fingers positioned adjacent the second end 154 of the trigger member 150 may have similar levels of force transferred to the trigger member 150 and/or the drive mechanism 160 due to the parallel and/or longitudinal motion of the trigger member 150. As a result, less fatigue and/or less stress may be noticed and/or felt by the user.

Figure 10:
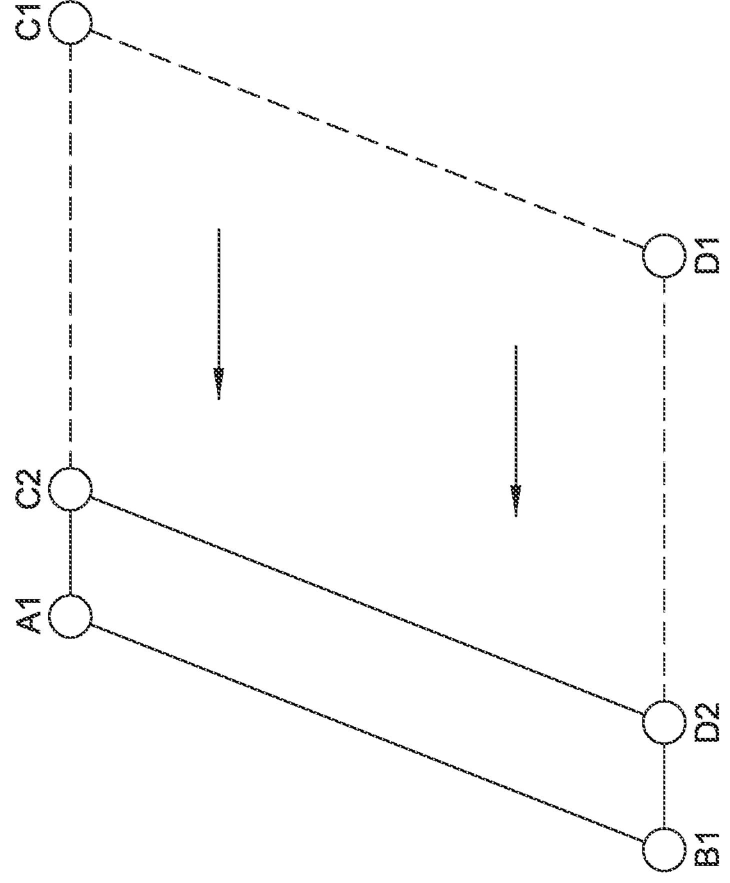
FIG. 10 schematically illustrates how the relative positioning of selected features of the disclosed tissue resection device changes during use.

FIG. 10 schematically illustrates how the reference points A, B, C, and D on the tissue resection device 100 move during operation of the trigger member 150. In an initial configuration or first position (e.g., the distalmost position) of the trigger member 150, the first end 142 (e.g., FIGS. 6-9) of the palm grip 140 may be located at position A1 and the second end 144 (e.g., FIGS. 6-9) of the palm grip 140 may be located at position B1, and the first end 152 (e.g., FIGS. 6-9) of the trigger member 150 may be located at position C1 and the second end 154 (e.g., FIGS. 6-9) of the trigger member 150 may be located at position D1. During operation, the first end 152 (e.g., FIGS. 6-9) of the trigger member 150 may be moved longitudinally toward the palm grip 140 and/or the second configuration, such that the first end 152 (e.g., FIGS. 6-9) of the trigger member 150 moves from position C1 to position C2. Similarly, the second end 154 (e.g., FIGS. 6-9) of the trigger member 150 may be moved longitudinally toward the palm grip 140 and/or the second configuration, such that the second end 154 (e.g., FIGS. 6-9) of the trigger member 150 moves from position D1 to position D2. As may be seen schematically in FIG. 10, the trigger member 150 (e.g., the longitudinal axis of the trigger member 150) denoted by line C1-D1 and/or C2-D2 remains substantially parallel with the palm grip 140 (e.g., the longitudinal axis of the palm grip 140) denoted by line A1-B1 as the trigger member 150 is actuated between the first position (e.g., the distalmost position) and the second position (e.g., the proximalmost position). Thus, translational movement of the trigger member 150 between the first position and the second position may be in a direction generally parallel to the central longitudinal axis 132 (e.g., FIGS. 6-9). Thus, the first end 152 (e.g., FIGS. 6-9) of the trigger member 150 may move the same distance (measured between points C1 and C2) as the second end 154 (e.g., FIGS. 6-9) of the trigger member 150 (measured between points D1 and D2) when being actuated between the first position and the second position during use. The oblique angle between the longitudinal axis (denoted by line C1-D1) of the trigger member 150 and the central longitudinal axis of the 132 may remain substantially constant when the trigger member 150 is translated longitudinally toward/away from the palm grip 140 in a direction parallel to the central longitudinal axis 132 between the first position (e.g., the distalmost position) and the second position (e.g., the proximalmost position). Thus, the path that the first end 152 (e.g., FIGS. 6-9) of the trigger member 150 follows when the trigger member 150 is actuated between the first position and the second position may be parallel to the central longitudinal axis 132, and the path that the second end 154 (e.g., FIGS. 6-9) of the trigger member 150 follows when the trigger member 150 is actuated between the first position and the second position may be parallel to the central longitudinal axis 132.

The materials that can be used for the various components of the tissue resection device and the various elements thereof disclosed herein may include those commonly associated with medical devices. For simplicity purposes, the following discussion refers to the device. However, this is not intended to limit the devices, components, and methods described herein, as the discussion may be applied to other elements, members, components, or devices disclosed herein, such as, but not limited to, the handle assembly, the handle, the elongate tubular body, the palm grip, the trigger member, the drive mechanism, the tissue resection element, the return spring, the resilient member, the elongate sheath, etc. and/or elements or components thereof.

In some embodiments, the device and/or components thereof may be made from a metal, metal alloy, polymer (some examples of which are disclosed below), a metal-polymer composite, ceramics, combinations thereof, and the like, or other suitable material.

Some examples of suitable polymers may include polytetrafluoroethylene (PTFE), ethylene tetrafluoroethylene (ETFE), fluorinated ethylene propylene (FEP), polyoxymethylene (POM), polyether block ester, polyurethane, polypropylene (PP), polyvinylchloride (PVC), polyether-ester, ether or ester based copolymers (for example, butylene/poly (alkylene ether) phthalate and/or other polyester elastomers), polyamide, elastomeric polyamides, block polyamide/ethers, polyether block amide (PEBA, for example available under the trade name PEBAX®), ethylene vinyl acetate copolymers (EVA), silicones, polyethylene (PE), high-density polyethylene, low-density polyethylene, linear low density polyethylene, polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide, polysulfone, nylon, nylon-12, perfluoro(propyl vinyl ether) (PFA), ethylene vinyl alcohol, polyolefin, polystyrene, epoxy, polyvinylidene chloride (PVdC), poly(styrene-b-isobutylene-b-styrene), polycarbonates, polyisobutylene (PM), polyisobutylene polyurethane (PIBU), polyurethane silicone copolymers, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear elastic and/or super-elastic nitinol; other nickel alloys such as nickel-chromium-molybdenum alloys, nickel-copper alloys, nickel-cobalt-chromium-molybdenum alloys, nickel-molybdenum alloys, other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys; platinum enriched stainless steel; titanium; combinations thereof; or any other suitable material.

In at least some embodiments, portions or all of the device and/or components thereof may also be doped with, made of, or otherwise include a radiopaque material. Radiopaque materials are understood to be materials capable of producing a relatively bright image on a fluoroscopy screen or another imaging technique during a medical procedure. This relatively bright image aids the user of the device in determining its location. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the device to achieve the same result.

In some embodiments, a degree of Magnetic Resonance Imaging (MRI) compatibility is imparted into the device and/or other elements disclosed herein. For example, the device and/or components or portions thereof may be made of a material that does not substantially distort the image and create substantial artifacts (i.e., gaps in the image). Certain ferromagnetic materials, for example, may not be suitable because they may create artifacts in an MRI image. The device or portions thereof may also be made from a material that the MRI machine can image. Some materials that exhibit these characteristics include, for example, tungsten, cobalt-chromium-molybdenum alloys, nickel-cobalt-chromium-molybdenum alloys, nitinol, and the like, and others.

In some embodiments, the device and/or other elements disclosed herein may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethyl ketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl ketone, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed:

1. A handle assembly for a tissue resection device, comprising:

a handle including:

an elongate tubular body defining a central longitudinal axis, and a palm grip having a first end coupled to the elongate tubular body, the palm grip extending from the elongate tubular body to a second end spaced apart from the elongate tubular body, the palm grip being configured to be engaged by a palm of a user;

a trigger member having a first end coupled to the elongate tubular body, the trigger member extending from the elongate tubular body to a second end spaced apart from the elongate tubular body, the trigger member being configured to be engaged by one or more fingers of the user; and a drive mechanism disposed within the elongate tubular body, the drive mechanism being configured to move a tissue resection element extending distally from the elongate tubular body;

wherein the trigger member is engaged with the drive mechanism such that translation of the trigger member relative to the handle actuates the drive mechanism;

wherein the first end and the second end of the trigger member are configured to translate in a first direction parallel to the central longitudinal axis between a first position that is a distalmost position and a second position that is a proximal most position;

wherein in the first position the first end and the second end of the trigger member are disposed distal of the palm grip;

further comprising a return spring disposed within the elongate tubular body, wherein the return spring biases the trigger member toward the first position; and further comprising a resilient member extending from the palm grip to the trigger member outside of the elongate tubular body.

2. The handle assembly of claim 1, wherein the resilient member is configured to bias the trigger member toward the first position.

3. The handle assembly of claim 1, wherein the trigger member is nonpivoting relative to the elongate tubular body.

4. The handle assembly of claim 1, wherein the trigger member is nonpivoting relative to the palm grip.

5. The handle assembly of claim 1, wherein the palm grip extends radially from the central longitudinal axis a first distance, and no other structure of the handle assembly extends radially from the central longitudinal axis more than the first distance.

6. The handle assembly of claim 1, wherein the drive mechanism is configured to rotate the tissue resection element.

7. The handle assembly of claim 1, wherein the drive mechanism is configured to axially translate the tissue resection element.

8. The handle assembly of claim 1, wherein the drive mechanism is configured to reciprocate the tissue resection element.

9. A tissue resection device, comprising:

a handle assembly, comprising:

a handle including:

an elongate tubular body defining a central longitudinal axis, and a palm grip extending from the elongate tubular body, the palm grip being configured to be engaged by a palm of a user;

a trigger member extending from the elongate tubular body, the trigger member being configured to be engaged by one or more fingers of the user;

a drive mechanism disposed within the elongate tubular body;

a return spring disposed within the elongate tubular body, wherein the return spring biases a first end of the trigger member in a distal direction toward a first position of the trigger member; and a resilient member extending from the palm grip to the trigger member outside of the elongate tubular body, wherein the resilient member biases a second end of the trigger member in the distal direction toward the first position of the trigger member; and a tissue resection element extending distally from the elongate tubular body;

wherein the drive mechanism is configured to move the tissue resection element relative to the handle;

wherein the trigger member is engaged with the drive mechanism such that translation of the trigger member relative to the handle actuates the drive mechanism, wherein the trigger member is non-pivotably coupled to the handle.

10. The tissue resection device of claim 9, wherein the trigger member is configured to translate parallel to the central longitudinal axis between the first position and a second position.

11. The tissue resection device of claim 9, wherein the return spring exerts a first force in the distal direction against the trigger member;

wherein the resilient member exerts a second force in the distal direction against the trigger member;

wherein the first force is within 5% of the second force.

12. The tissue resection device of claim 11, wherein the first force is substantially equal to the second force.

13. A handle assembly for a tissue resection device, comprising:

a handle including:

an elongate tubular body defining a central longitudinal axis, and a palm grip extending from the elongate tubular body, the palm grip being configured to be engaged by a palm of a user;

a trigger member non-pivotably coupled to the handle, the trigger member being configured to be engaged by one or more fingers of the user;

a drive mechanism disposed within the elongate tubular body, the drive mechanism being configured to move a tissue resection element extending distally from the elongate tubular body;

a resilient member disposed outside of the elongate tubular body and coupled to the palm grip and the trigger member, wherein the resilient member biases the trigger member away from the palm grip; and a return spring disposed within the elongate tubular body, wherein the return spring biases the trigger member away from the palm grip;

wherein the trigger member is engaged with the drive mechanism such that translation of the trigger member along the central longitudinal axis actuates the drive mechanism;

wherein the resilient member comprises a first end fixedly attached to the palm grip, a second end fixedly attached to the trigger member, and a body portion configured to move radially relative to the central longitudinal axis as the trigger member is translated along the central longitudinal axis.

14. The handle assembly of claim 13, wherein the trigger member is configured to translate in a direction parallel to the central longitudinal axis.

15. The handle assembly of claim 13, wherein the resilient member is configured to balance force exerted on the trigger member by the return spring.

16. The handle assembly of claim 13, wherein the drive mechanism is configured to reciprocate a tissue resection element extending distally from the elongate tubular body.

17. The handle assembly of claim 13, wherein the trigger member extends at an oblique angle to the central longitudinal axis and the oblique angle remains generally constant when the trigger member is translated along the central longitudinal axis.

* * * * *